United States Patent [19]

Lippman

[11] Patent Number: 5,073,163
[45] Date of Patent: Dec. 17, 1991

[54] APPARATUS FOR TREATING GLAUCOMA

[76] Inventor: Myron E. Lippman, 824 Alston Rd., Santa Barbara, Calif. 93108

[21] Appl. No.: 471,779

[22] Filed: Jan. 29, 1990

[51] Int. Cl.$^5$ .............................................. A61M 5/00
[52] U.S. Cl. ...................................................... 604/9
[58] Field of Search ....................................... 604/8–10, 604/22, 126, 252, 294; 55/159; 137/497; 138/44

[56] References Cited

U.S. PATENT DOCUMENTS

| | | | |
|---|---|---|---|
| 4,200,096 | 4/1980 | Charvin | 55/159 |
| 4,554,918 | 11/1985 | White | 604/10 |
| 4,604,087 | 8/1986 | Joseph | 604/294 |
| 4,729,761 | 3/1988 | White | 604/8 |
| 4,750,901 | 6/1988 | Molteno | 604/8 |
| 4,787,885 | 11/1988 | Binder | 604/8 |
| 4,886,488 | 12/1989 | White | 604/9 |

Primary Examiner—C. Fred Rosenbaum
Assistant Examiner—William W. Lewis
Attorney, Agent, or Firm—Jack C. Munro

[57] ABSTRACT

An apparatus for treating glaucoma which can be mounted directly onto the outer surface of the eyeball with a portion of the apparatus to connect with the interior of the eyeball. The apparatus includes a plastic block including a plurality of tiny through openings. Liquid from the interior of the eyeball is to seep through the openings in the plastic block to relieve excess pressure within the eyeball. This leakage is to occur only when the pressure level within the eyeball exceeds a predetermined level.

9 Claims, 2 Drawing Sheets

APPARATUS FOR TREATING GLAUCOMA

REFERENCE TO PRIOR APPLICATION

The subject application is a substitute application of patent application Ser. No. 07/234,534, filed Aug. 22, 1988, by the same title and by the same inventor and now abandoned.

BACKGROUND OF THE INVENTION

The field of this invention has to do with medicine and more particularly to an apparatus which is to be mounted in conjunction with an eyeball to provide for a continuous source for relief of pressure of the liquid contained within the eyeball to prevent that liquid from exceeding a pre-established pressure level.

A common disease of the eye is glaucoma. Within the eyeball is located a liquid called the aqueous humor and vitreous humor. This liquid is normally under a certain pressure with the common pressure being approximately twenty millimiters of mercury. In glaucoma, this pressure increases and if the pressure gets too severe, the individual can go blind.

In the past, there have been different techniques to relieve this excessive pressure and a vast amount of money is spent each year on drops that are to be placed onto the eye that are minimally effective. Additionally, there have been numerous surgical techniques in order to relieve this pressure. One of the most common surgical techniques is to cut a hole in the eyeball which provides an outlet for some of the liquid contained in the eyeball thereby relieving the pressure. This hole is then sutured. The disadvantage of this technique is that initially the pressure of the liquid in the eyeball is decreased below the desired level to atmospheric pressure this lack of pressure within the eyeball can cause certain undesirable medical problems such as corneal dystrophy as well as other problems. As time goes on, normally the pressure will again build back to its original adverse level which will require duplicating of the surgical procedure or initiating some other procedure.

To overcome the disadvantage of this technique there has been manufactured a valve assembly which is to be mounted in conjunction with the eyeball and located within the hole cut into the eyeball. It is the function of this valve to be activated if a certain pressure level is exceeded and provide an escape route for some of the liquid contained within the eyeball thereby releasing the pressure. The disadvantage of this valve is that it frequently malfunctions thereby requiring replacement or removal of the valve unit.

Another known device has to do with utilizing a balloon operating a pump and check valve as opposed to sole use of a check valve. This pump is to release liquid when pressure is applied to the balloon. This pressure to the balloon is to be applied by the natural blinking process of a human being or is to be applied by manual rubbing of one's eye. Again, this type of unit is not free from malfunction.

There is a need to construct an improved form of pressure relieving device which is to be mounted in conjunction with an eyeball which will continually release the pressure of an eyeball once the pressure has exceeded a predetermined level with this device being substantially free of malfunction having no moving parts, valves or pumps.

SUMMARY OF THE INVENTION

The basis of the subject matter of this invention has to do with utilization of a tiny block of plastic within which is located a mass of tiny through openings. This block is located to separate the pressurized liquid from the ambient. These openings are so tiny that it will be necessary for the liquid to exceed a certain pre-established pressure level in order for leaking of the liquid to be initiated through the openings. In other words, in conjunction with this invention, the size of the openings can be pre-established to require that the pressure level of liquid exceed twenty millimeters of mercury in order for adequate leakage to begin. If the pressure level begins to drop below the twenty millimeters of mercury, the leakage stops. This block is to be mounted within a flexible rubber housing. This housing is to include a tubular extension. Side flanges are mounted on the exterior of the housing in order to facilitate suturing of the housing onto an eyeball.

The primary objective of the present invention is to provide for pressure relief of the interior of the eyeball of a human being without including any moving parts in conjunction with a pressure relief apparatus thereby substantially eliminating any possibility of malfunction of the apparatus once installed.

Another objective of the present invention is to construct an apparatus which can be simply and quickly installed in position in conjunction with the eyeball thereby minimizing the difficulty of the operative technique.

DETAILED DESCRIPTION OF THE SHOWN EMBODIMENT

Figure 2:
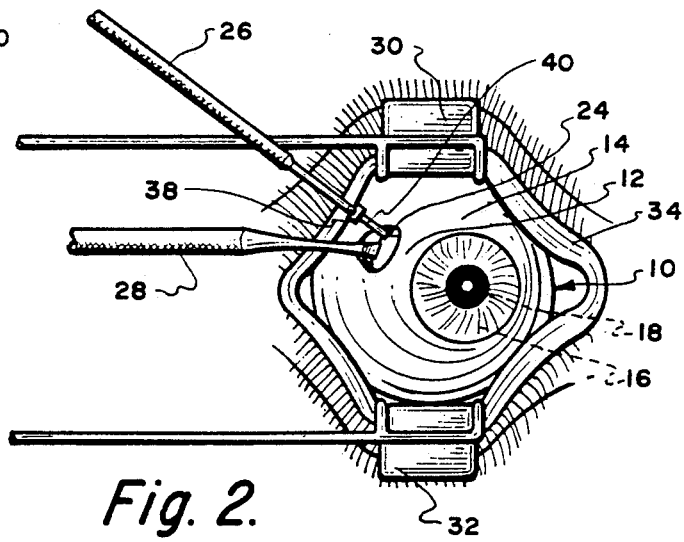
FIG. 2 is a diagrammatic view depicting installation of the apparatus of the present invention in conjunction with an eyeball.
Figure 3:
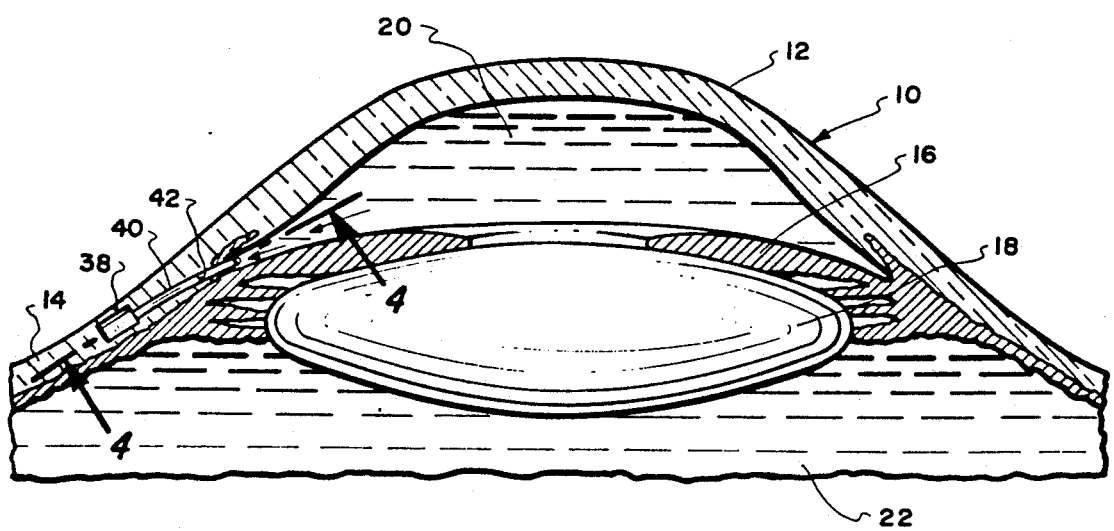
FIG. 3 is a cross-sectional view through an eyeball showing the approximate position of the apparatus of the present invention.

Referring particularly to FIGS. 2 and 3 of the drawings, there is depicted a portion of an eyeball 10 which has a cornea 12. Surrounding the cornea 12 is the white of the eye, which is known as the sclera 14. Within the interior of the eyeball, there is located an iris 16 which surrounds a lens 18. Located between the lens 18 and the cornea 12 is a liquid known as the aqueous humor 20. Located interiorly of the sclera 14 is a liquid known as vitreous humor 22.

A surgical incision 24 is to be made in the sclera 14 by means of appropriate medical, surgical instruments 26 and 28. When making the incision 24, tools 30 and 32 are utilized to spread apart the eyelid 34 to expose the sclera 14 as much as possible to facilitate the making of the incision 24. The incision 24 is made in such a manner to produce a flap (not shown) of the sclera 14. Within the incision area there is to be located the apparatus 36 of this invention.

Figure 1:
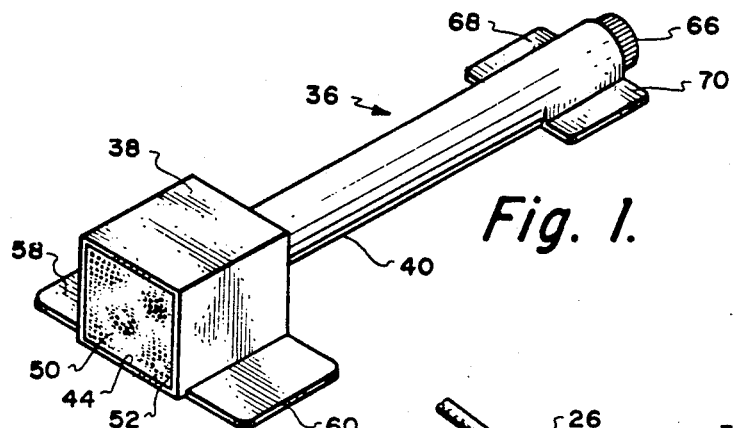
FIG. 1 is an isometric view of the apparatus of the present invention.
Figure 4:
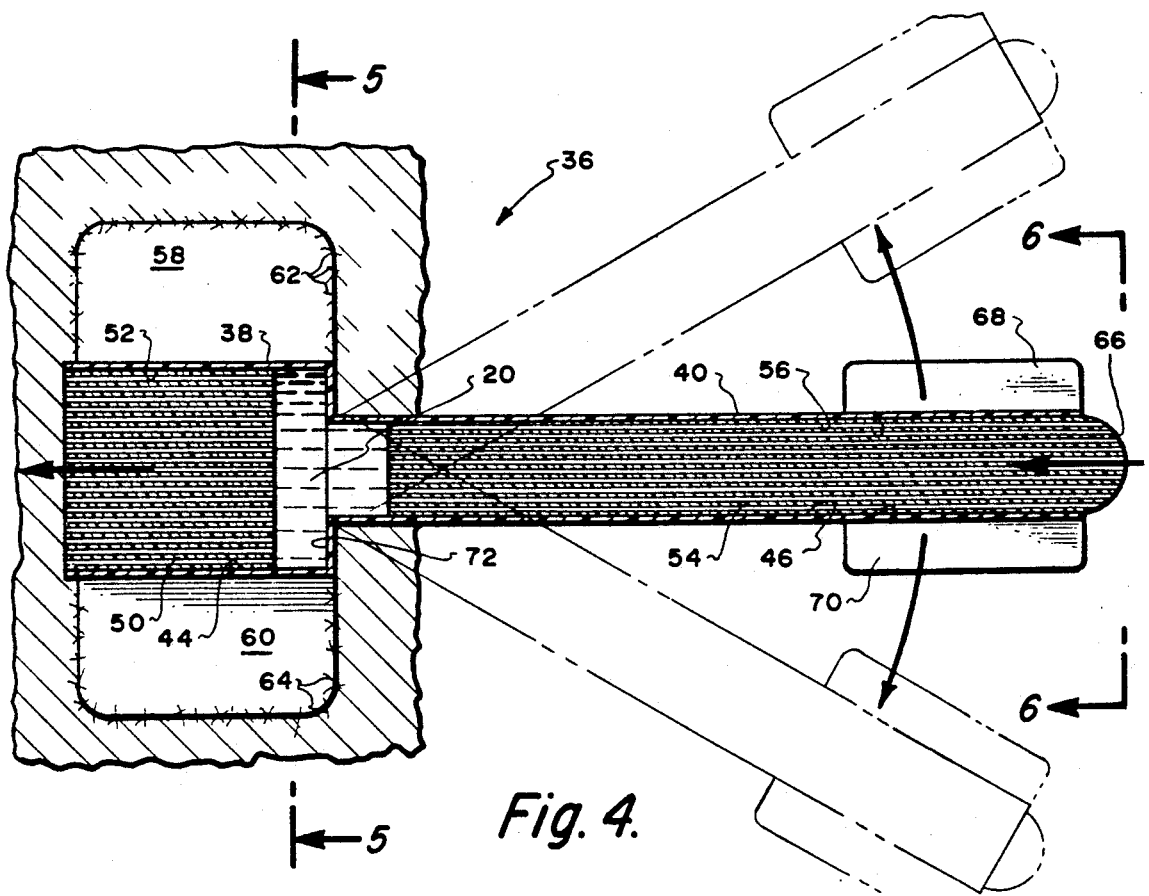
FIG. 4 is a longitudinal, cross-sectional view of the apparatus of this invention taken along line 4—4 of FIG. 3.
Figure 5:
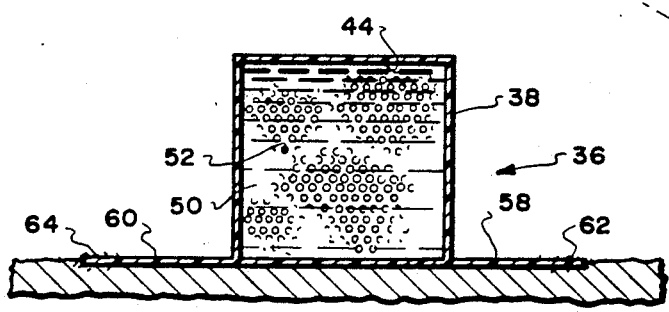
FIG. 5 is a lateral, cross-sectional view of the apparatus of this invention taken along line 5—5 of FIG. 4.
Figure 6:
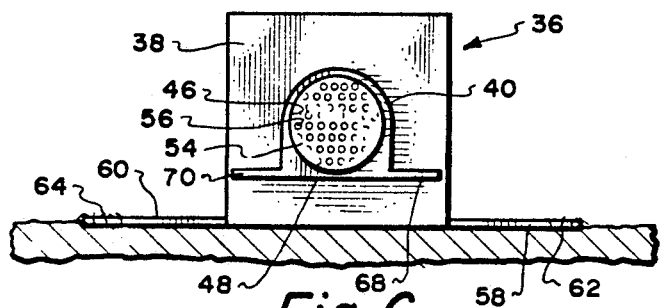
FIG. 6 is a front end view of the apparatus of this invention taken along line 6—6 of FIG. 4.

Apparatus 36 is formed of a housing defined by a main section housing 38 and a tubular extension 40. Both the main section housing 38 and tubular extension 40 are constructed of the same material and are integrally connected together. The preferable material would be a rubber and a pliable rubber. Although, the apparatus 36 will assume an at-rest position as shown in FIG. 1, the apparatus is readily bendable so that the tubular extension 40 can be easily pivoted relative to the main section housing 38 with this pivoting action being clearly shown in the phantom lines in FIG. 4. The reason for this bending is so the tubular extension 40 can be inserted through a hole 42 which has been cut through the sclera 14 of the eyeball 10 into the cavity occupied by the aqueous humor 20. Also, some physicians may make the hole 42 into the chamber occupied by the vitreous humor 22.

The main section housing 38 includes an interior chamber 44. The tubular extension 40 includes a cylindrical interior chamber 46. The exterior bottom edge of the tubular extension 40 is formed as a flat wall 48. This flat wall 48 facilitates the locating of the tubular extension 30 against the sclera 14 that was cut by the incision 24.

Within the chamber 44 is located a plastic block 50. This plastic block 50 has a mass of tiny, through openings 52. These openings 52, in all probability, will not exceed one-thousandth of an inch. The block 50 may be probably no greater than one-eighth of an inch square and may well be in the range of one-sixteenth of an inch square. It is estimated that there will be approximately two hundred twenty-five of the openings 52 formed within the block 50.

There may be utilized within the interior chamber 46 a cylindrical plastic block 54. Within this block 54 there is similarly included a mass of tiny, through openings 56. The size of the openings 56 are basically identical to the size of the openings 52. The material of construction for the cylindrical block 54 will generally be the same as the material of construction of the block 50. In some instances, it may be found to be desirable to not utilize the block 54, but use only block 50.

Extending laterally from one side of the main section housing 38 is a mounting flange 58. A similar mounting flange 60 is attached to the opposite side of the main section housing 38 and extends laterally therefrom. The length of the flanges 58 and 60 are identical as is also their overall size. Normally, the approximate length of the flanges 58 and 60 will be about one-tenth of an inch. The length of the flanges 58 and 60 is just slightly less than the overall length of the main section housing 38 which is generally in the range of one hundred twenty thousandths of an inch.

Suturing is to occur between the sclera 14 and the flanges 58 and 60 to securely mount in place the main section housing 38. This suturing is shown as stitches 62 of flange 58 and stitches 64 for flange 60.

The outer end of the cylindrical block 54 is beveled into a rounded surface 66. This rounded 66 protrudes slightly from the end of the tubular extension 40. This rounded end 66 will actually be located within the interior of the eyeball 10 when it is properly positioned and in direct contact with either the aqueous humor 20 or the vitreous humor 22.

The reason for the bending of the tubular extension 40 relative to the main section housing 38 is so that it facilitates manual maneuverability to permit insertion of tubular extension 40 in the proper position. Once the proper position is obtained, it is desired to fix in position the tubular extension 40 onto the eyeball 10. Protruding laterally from one side of the tubular extension 40 is a mounting flange 68 with a similar mounting flange 70 being integrally connected to the opposite side of the tubular extension 40. These flanges 68 and 70 are, again, for the purpose to be sutured directly to the sclera 14 thereby fixing the precise position of the tubular extension 40.

The flap in the sclera 14 that was produced by the incision 24 is now stretched over the extension 40 and the main section housing 38 and is sutured in place. Because of the smallness of the apparatus 36 of this invention, there will only remain a slight bulge that possibly would be observed if one looked closely at the eyeball 10. Upon pressure exceeding the twenty millimeters of mercury of the aqueous humor 20, and the rounded end 66 is located in conjunction with the aqueous humor 20, liquid will be conducted through the openings 56 filling the chamber 72 and then through the openings 52 and deposited near the exterior surface of the sclera 14. This liquid will then be conducted through the body of the human being and disposed of in a normal manner as waste.

What is claimed is:

1. An apparatus for treating glaucoma comprising:
a housing having a longitudinal center axis, said housing having a main section and a tubular extension, said tubular extension having an open outer end, said tubular extension connecting with said main section, said tubular extension being hollow defining a connecting chamber, said main section being hollow defining a main chamber, said connecting chamber connecting with said main chamber, said main chamber having an open aft end;
a rigid plastic block located within said housing, said rigid plastic block closely conforming in a fluid tight manner to said housing, said rigid plastic block having a plurality of tiny through openings located in a parallel spaced-apart arrangement, each said through opening having a diameter no greater than one thousandth of an inch and a length of at least one-sixteenth of an inch, said through openings cause sufficient restriction to passage of a liquid therethrough to be able to maintain a pressure differential of approximately twenty millimeters of mercury between the liquid and the ambient.

2. The apparatus as defined in claim 1 wherein:
said housing being constructed of a bendable material, said tubular extension being capable of limited pivoting movement relative to said main section.

3. The apparatus as defined in claim 2 wherein:
said main chamber being larger in cross-section than said extension in cross-section.

4. The apparatus as defined in claim 3 wherein:
said main section having a pair of side extending flanges mounted on the exterior surface of the main section, said side extending flanges facilitating suturing of said main section to an eyeball.

5. The apparatus as defined in claim 1 wherein:
said rigid plastic block being located within said main chamber.

6. The apparatus as defined in claim 1 wherein:
the longitudinal dimension of through openings being located substantially parallel to said longitudinal center axis.

7. The apparatus as defined in claim 1 wherein:
said rigid plastic block being divided into a first part and a second part, said first part being mounted within said main chamber, said second part being located within said connecting chamber.

8. An apparatus for treating glaucoma comprising:

a housing having a longitudinal center axis, said housing having a main section and a tubular extension, said tubular extension having an open outer end, said tubular extension connecting with said main section, said tubular extension being hollow defining a connecting chamber, said main section being hollow defining a main chamber, said connecting chamber connecting with said main chamber, said main chamber having an open aft end;

a rigid block located within said housing, said rigid block closely conforming in a fluid tight manner to said housing, said rigid block having a plurality of tiny through openings, each said through opening having a diameter no greater than one thousandth of an inch, said through openings cause sufficient restriction to passage of a liquid therethrough to be able to maintain a pressure differential of approximately twenty millimiters of mercury between the liquid and the ambient;

said housing being constructed of a bendable material, said tubular extension being capable of limited pivoting movement relative to said main section;

said main chamber being larger in cross-section than said extension in cross-section;

said main section having a pair of side extending flanges mounted on the exterior surface of the main section, said side extending flanges facilitating suturing of said main section to an eyeball; and a second set of side flanges being attached to said tubular extension extending outwardly therefrom, said second set of side flanges facilitating suturing to an eyeball.

9. The apparatus as defined in claim 8 wherein:
said rigid plastic block being divided into a first part and a second part, said first part being mounted within said main chamber, said second part being located within said connecting chamber.

* * * * *